United States Patent [19]
Lev

[11] Patent Number: 6,066,153
[45] Date of Patent: May 23, 2000

[54] DEVICE AND METHOD FOR RESECTING BODY TISSUES

[76] Inventor: Avigdor Lev, 27 Kaplanski, 49213 Neve Uz, Petach Tikva, Israel

[21] Appl. No.: 09/282,168

[22] Filed: Mar. 31, 1999

[51] Int. Cl.[7] .................................................... A61B 17/14
[52] U.S. Cl. .............................................................. 606/180
[58] Field of Search ............................ 606/80, 159, 170, 606/180, 171, 27, 107; 600/562, 564, 565; 604/22

[56] References Cited

U.S. PATENT DOCUMENTS

| | | | |
|---|---|---|---|
| 2,729,210 | 1/1956 | Spencer | 600/564 |
| 3,526,219 | 9/1970 | Balamuth . | |
| 3,777,743 | 12/1973 | Binard et al. . | |
| 4,308,875 | 1/1982 | Young . | |
| 4,750,488 | 6/1988 | Wuchinich et al. . | |
| 4,815,461 | 3/1989 | Rodriguez . | |
| 4,857,045 | 8/1989 | Rydell | 606/159 |
| 4,867,157 | 9/1989 | McGurk-Burleson et al. | 606/170 |
| 5,092,872 | 3/1992 | Segalowitz | 606/159 |
| 5,100,426 | 3/1992 | Nixon | 606/159 |
| 5,135,531 | 8/1992 | Shiber | 606/159 |
| 5,257,632 | 11/1993 | Turkel et al. . | |
| 5,267,955 | 12/1993 | Hanson | 604/22 |
| 5,269,785 | 12/1993 | Bonutti | 606/80 |
| 5,318,576 | 6/1994 | Plassche, Jr. et al. | 606/159 |
| 5,354,311 | 10/1994 | Kambin et al. | 606/170 |
| 5,358,472 | 10/1994 | Vance et al. | 606/159 |
| 5,406,959 | 4/1995 | Mann . | |
| 5,624,452 | 4/1997 | Yates | 606/27 |
| 5,632,755 | 5/1997 | Nordgren et al. | 606/159 |
| 5,643,304 | 7/1997 | Schechter et al. . | |
| 5,669,876 | 9/1997 | Schechter et al. . | |
| 5,685,840 | 11/1997 | Schechter et al. . | |
| 5,876,414 | 3/1999 | Straub | 606/159 |

*Primary Examiner*—Jeffrey A. Smith
*Assistant Examiner*—Eduardo C. Robert
*Attorney, Agent, or Firm*—Mark M. Friedman

[57] ABSTRACT

A resecting device for use in tissue removal is disclosed. The resecting device includes a cannula having a hollow and which is sized for introduction into a body. The cannula is formed with at least one, preferably a plurality of, cutting openings each having a cutting edge. The resecting device further includes a rotating mechanism which is connectable through a shaft to the cannula and which serves for rotating the cannula around a longitudinal axis thereof. As a result of such rotation and the cannula's construction, when the cannula is contacted with a tissue, the cutting edges of the cutting openings dissect the tissue and direct the dissected tissue through the openings into the hollow of the cannula.

48 Claims, 11 Drawing Sheets

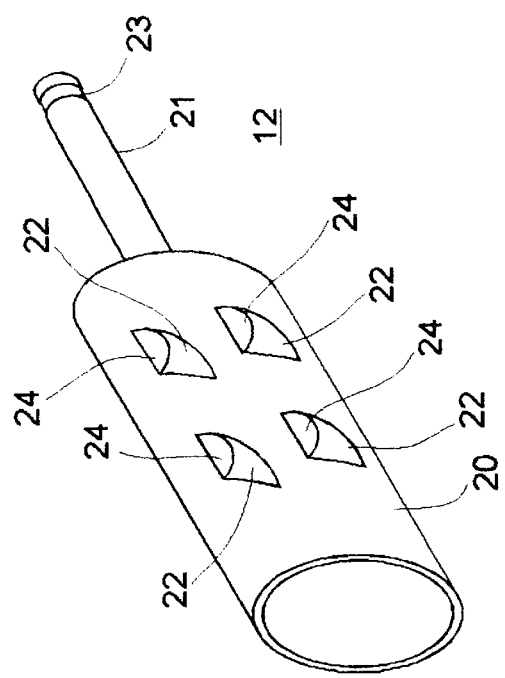
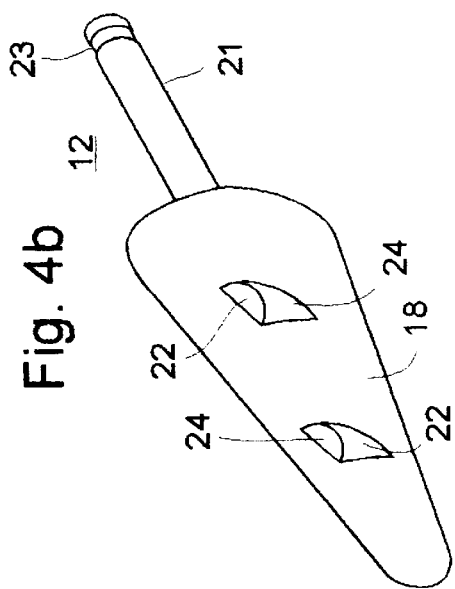
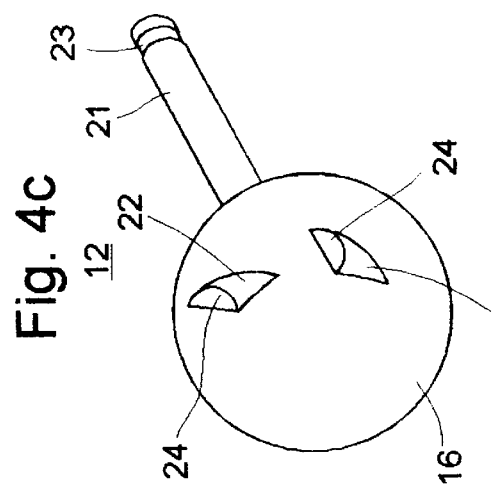
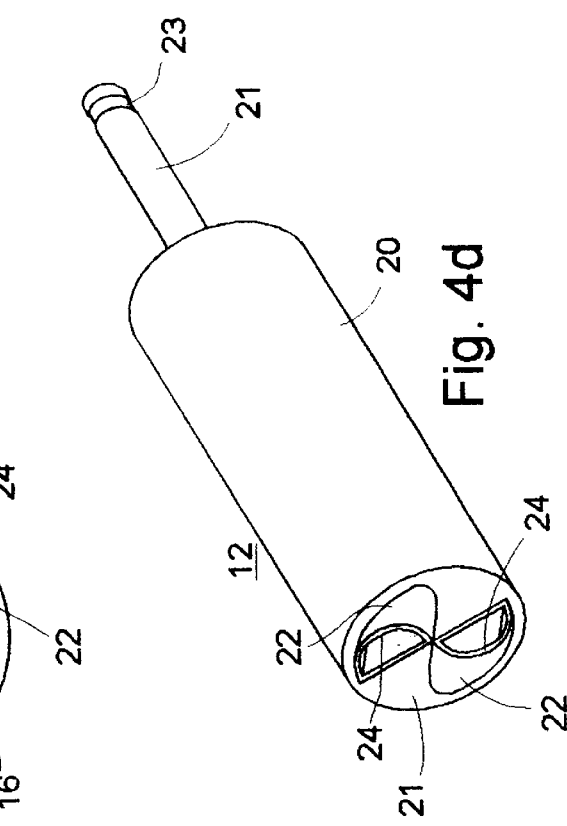
Fig. 4a
Fig. 4b
Fig. 4c
Fig. 4d

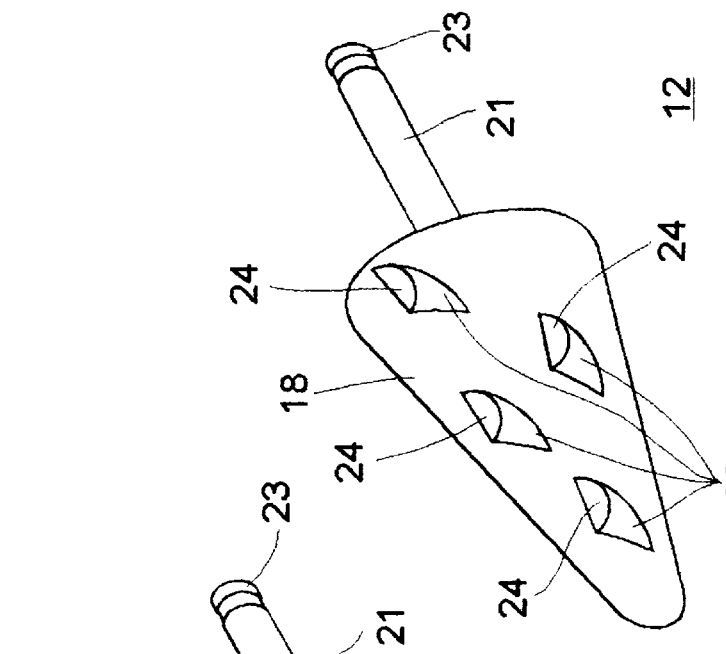
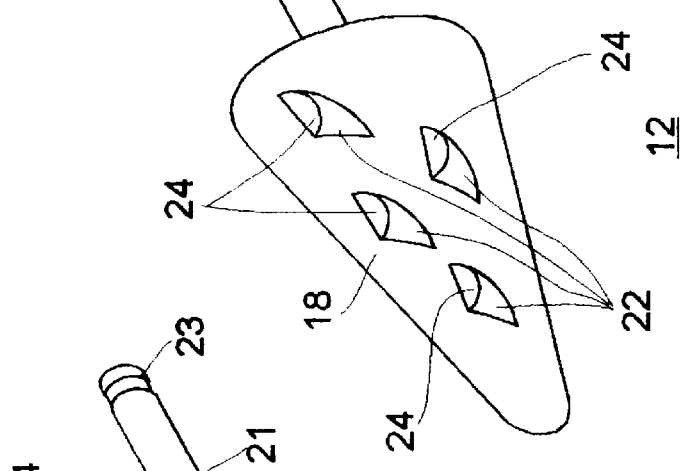
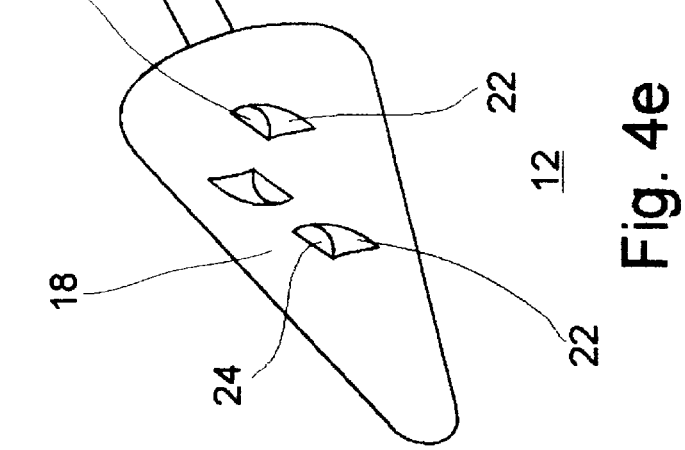

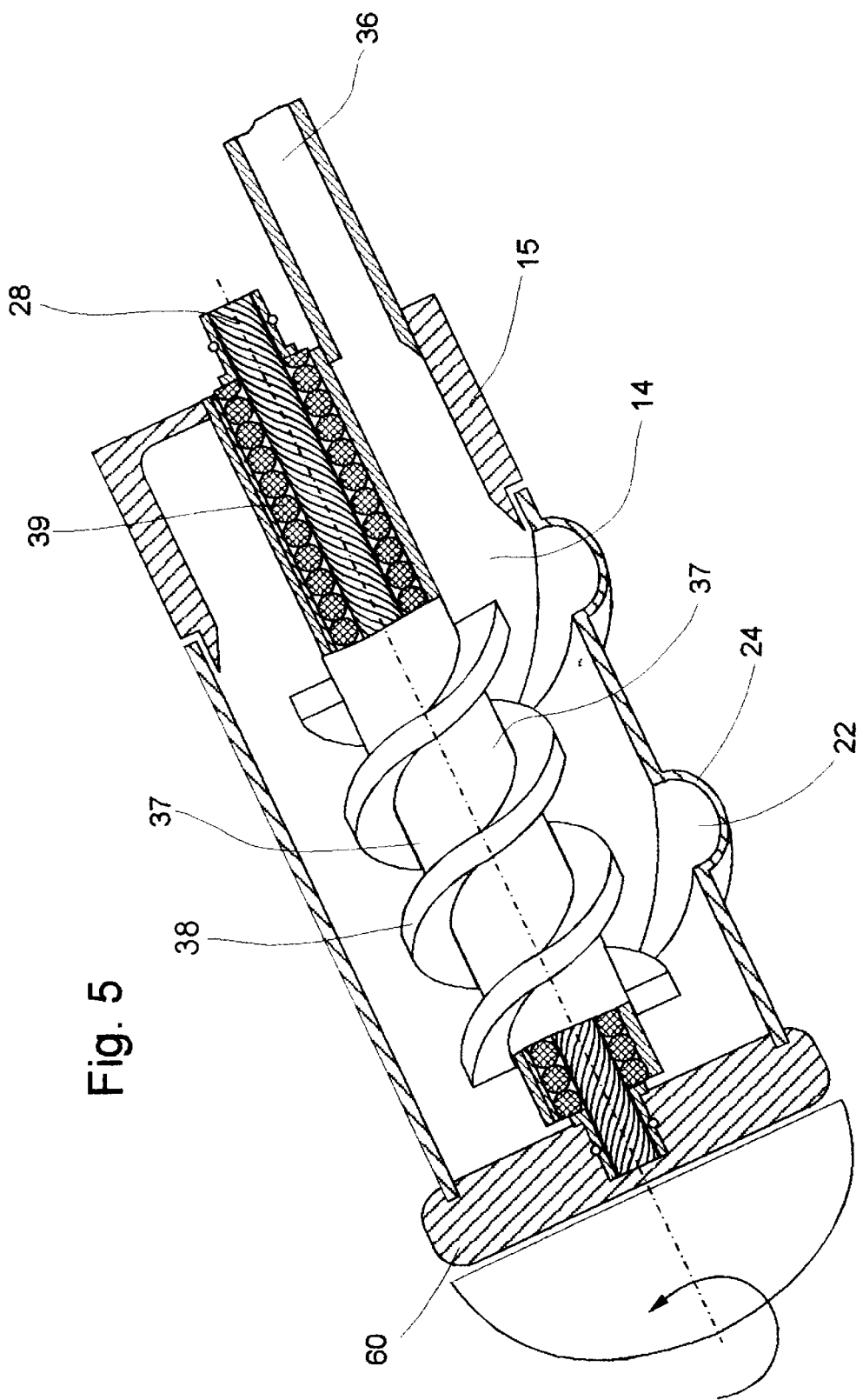

DEVICE AND METHOD FOR RESECTING BODY TISSUES

FIELD AND BACKGROUND OF THE INVENTION

The present invention relates to a resecting device and method for excision and removal of tissue from a patient's body and, more particularly, to a resecting cannula formed with resecting teeth and a hollow, and provided with rotary motion, such that when operated to rotate and contacted with a tissue, the tissue is excised into, and retained within, the hollow of the cannula. In addition, the device in accordance with prefenred embodiments of the teachings of the present invention is provided with a heating device, such that blood homeostasis can be effected, and/or with a dedicated mechanism for collecting the resected tissue for later analysis.

Modem surgical procedures have been utilized by the medical field for decades to diagnose and repair a variety of conditions. Due to the high risk associated with the highly invasive techniques utilized by surgical procedures, the medical field has adapted procedures and devices which utilize minimally invasive techniques. As such, these devices are designed to effect treatment to various body regions through minimal invasion and trauma to the patient's body.

Furthermore, when required, such devices can also be employed to collect tissue specimen from the region of treatment. For example, by utilizing such devices, tissue excision and collection from a patient's body of, for example, tumorous tissue can be effected, such that the tissue removed is collected and examined.

Further examples of procedures utilizing such devices include removal of the prostate in urological procedures, removal of the ovaries and lesions in gynecological procedures, removal of the gallbladder and kidney/gall stones in gastrointestinal procedures, removal of plaques in cardiovascular procedures, and ophthalmologic procedures for treatment of cataracts.

As such, various tissue removal devices and systems such as resectors and rasps have been devised within the last decade to perform diseconomy procedures.

One such device is employed in the field of neurosurgery, and is used specifically for the removal of tumors, blood clots, lesions, aneurysms or membranes. This device is described in U.S. Reissue Pat. No. 33,258 to Onik. According to Onik, tissue to be removed is drawn by suction into a central bore of an outer cutting sleeve. A pneumatically driven inner cutting sleeve operates as a guillotine to resect the tissue. The tissue is suspended in a saline irrigation fluid which also assists in aspiration of the resected tissue through the inner cutting sleeve.

Another example of a resecting device is disclosed in U.S. Pat. No. 5,643,304 to Schechter. This device includes a reciprocating blade which employs an adjustable reciprocating frequency, such that the frequency employed by the device can be tuned to match the target tissue(s).

While the experiences with this and other similar devices for percutaneous diseconomy have been favorable, there is naturally room for improvements in devices and methods for minimally invasive tissue removal.

The procedures using these devices are less invasive than prior surgical techniques, but there is still a need to reduce the amount of time required to perform the procedures and similar surgeries. Faster tissue removal translates to quicker procedures, reduced invasion and as such a reduced risk of trauma. In addition, as with any procedure involving body tissue excision employing prior art devices, there remains a risk of resecting desirable tissue as opposed to undesirable tissue sought to be removed. Finally, although all surgical techniques involve some trauma to surrounding tissue, there is a clear need to reduce even further the amount of trauma associated with such procedures.

At present, tissue removal devices which generally involve the use of motorized pneumatically driven guillotine, reciprocating blade, or rotary type cutters suffer from several shortcomings. One problem characteristic of these devices is that tissue is often torn, rather than sliced cleanly. In addition, with rotary cutters currently employed, the tissue has a tendency to become "spooled" or wound around the cutter or its drive shaft, thereby clogging or stalling the cutter.

Furthermore, with guillotine or reciprocating blade cutters accurate tissue removal of small tumorous tissue, or alternatively, rapid tissue removal of large tumor masses cannot be effected efficiently.

In addition, cannulas possessing either guillotine or reciprocating blade cutter mechanisms can only excise tissue of a shape resectable by such cutting blade mechanisms, and as such, these devices are implementable within a narrow range of resection applications.

Finally, currently employed resection devices are not provided with a built-in heating device effective in blood homeostasis, even though resection of vascularized tissues can cause a great deal of hemorrhaging, As such, the above mentioned features of the prior art devices lead to inherent limitations which impede such devices from effecting a rapid and accurate removal of various tissue types.

There is thus a widely recognized need for, and it would be highly advantageous to have, a tissue resecting device devoid of the above limitations.

SUMMARY OF THE INVENTION

According to the present invention there is provided a resecting device for use in tissue removal, comprising (a) a cannula having a hollow and a longitudinal axis, the cannula being sized for introduction into a body and formed with at least one cutting opening having a cutting edge; and (b) a rotating mechanism connectable through a shaft to the cannula for rotating the cannula around the longitudinal axis thereof, such that when contacted with a tissue and rotated, the cutting edge of the at least one cutting opening dissects the tissue and directs the dissected tissue through the opening and into the hollow of the cannula.

According to another aspect of the present invention there is provided a surgical procedure of tissue excision in a preselected region in a body, the procedure comprising the steps of (a) providing a resecting device, including a cannula having a hollow and a longitudinal axis, the cannula being sized for introduction into the body and being formed with at least one cutting opening having a cutting edge; (b) inserting the cannula into the preselected region in the body; and (c) contacting the cannula with a tissue to be excised and rotating the cannula via a rotating mechanism, such that the cutting edge of the at least one cutting opening dissects the tissue and directs the dissected tissue through the opening and into the hollow.

According to further features in preferred embodiments of the invention described below, the surgical procedure is selected from the group consisting of a urological procedure, a gynecological procedure, a gastrointestinal procedure, a cardiovascular procedure, a neurological procedure and an ophthalmologic procedure.

According to still further features in the described preferred embodiments the rotating mechanism is for rotating the cannula in reciprocal rotary motion.

According to still further features in the described preferred embodiments the cannula is forced with at least two cutting openings, the at least two cutting openings are positioned in an opposing configuration on at least a portion of the cannula.

According to still further features in the described preferred embodiments the resecting device further comprises a non-rotating protective sleeve covering at least a portion of the shaft.

According to still further features in the described preferred embodiments the resecting device further comprises a handpiece, the handpiece being for guiding the cannula into a preselected region of the body.

According to still further features in the described preferred embodiments the resecting device further comprises a tissue collecting chamber, the chamber being in fluid communication with the hollow such that tissue collected in the hollow is transportable to the chamber.

According to still further features in the described preferred embodiments the tissue collecting chamber is in fluid communication with the hollow through a channel formed within the shaft.

According to still further features in the described preferred embodiments the tissue collection chamber is in fluid communication with the hollow through a tube.

According to still further features in the described preferred embodiments the resecting device further comprises a conveying mechanism in the hollow of the cannula, the conveying mechanism being for conveying the dissected tissue within the cannula or from the cannula to the collecting chamber, if present.

According to still further features in the described preferred embodiments the conveying mechanism includes an Archimedes screw.

According to still further features in the described preferred embodiments the Archimedes screw is counter rotatable relative to the cannula.

According to still further features in the described preferred embodiments the Archimedes screw is stationary.

According to still further features in the described preferred embodiments the resecting device further comprises a pump, the pump being in fluid communication with the collecting chamber and being for pumping the dissected tissue from the cannula and into the collecting chamber.

According to still further features in the described preferred embodiments the handpiece includes a motor connected to the shaft, the motor serves for rotating the cannula.

According to still further features in the described preferred embodiments the resecting device further comprises an imaging system for intrabody monitoring a procedure being effected by the resecting device.

According to still further features in the described preferred embodiments invention both the sleeve and the shaft are flexible, so as to assist in spatial positioning of the cannula in the body.

According to still further features in the described preferred embodiments the cannula is formed with a plurality of cutting openings, the plurality of cutting openings are circumferencely positioned on at least a portion of the cannula.

According to still further features in the described preferred embodiments the cannula has a shape selected from the group consisting of a cone-shape, a cylindrical shape and a spherical shape.

According to still further features in the described preferred embodiments the resecting device further comprises a heating device, the heating device being for heating the tissue.

According to still further features in the described preferred embodiments the heating device includes a friction element, the friction element is contactable with a portion of the cannula, so as to generate heat thereat.

According to still further features in the described preferred embodiments the heating device includes a heating wire.

According to still further features in the described preferred embodiments the resecting device further comprises a temperature sensor for sensing the heat.

The present invention successfully addresses the shortcomings of the presently known configurations by providing a resecting device which is highly effective in tissue removal and collection.

BRIEF DESCRIPTION OF THE DRAWINGS

The invention is herein described, by way of example only, with reference to the accompanying drawings, wherein:

FIG. 2a.1 is a perspective view of a resecting device, according to another embodiment of the present invention;

FIG. 2a.2 is a perspective cutaway view of the cannula shown in FIG. 2a.1;

FIG. 2b is a magnification of a distal portion of the cannula of FIG. 2a;

FIGS. 4a–g are perspective views of some cannula forms used by the present invention;

FIG. 5 is a cross sectional view of a cannula including an Archimedes screw according to still another embodiment of the present invention;

DESCRIPTION OF THE PREFERRED EMBODIMENTS

Figure 1:
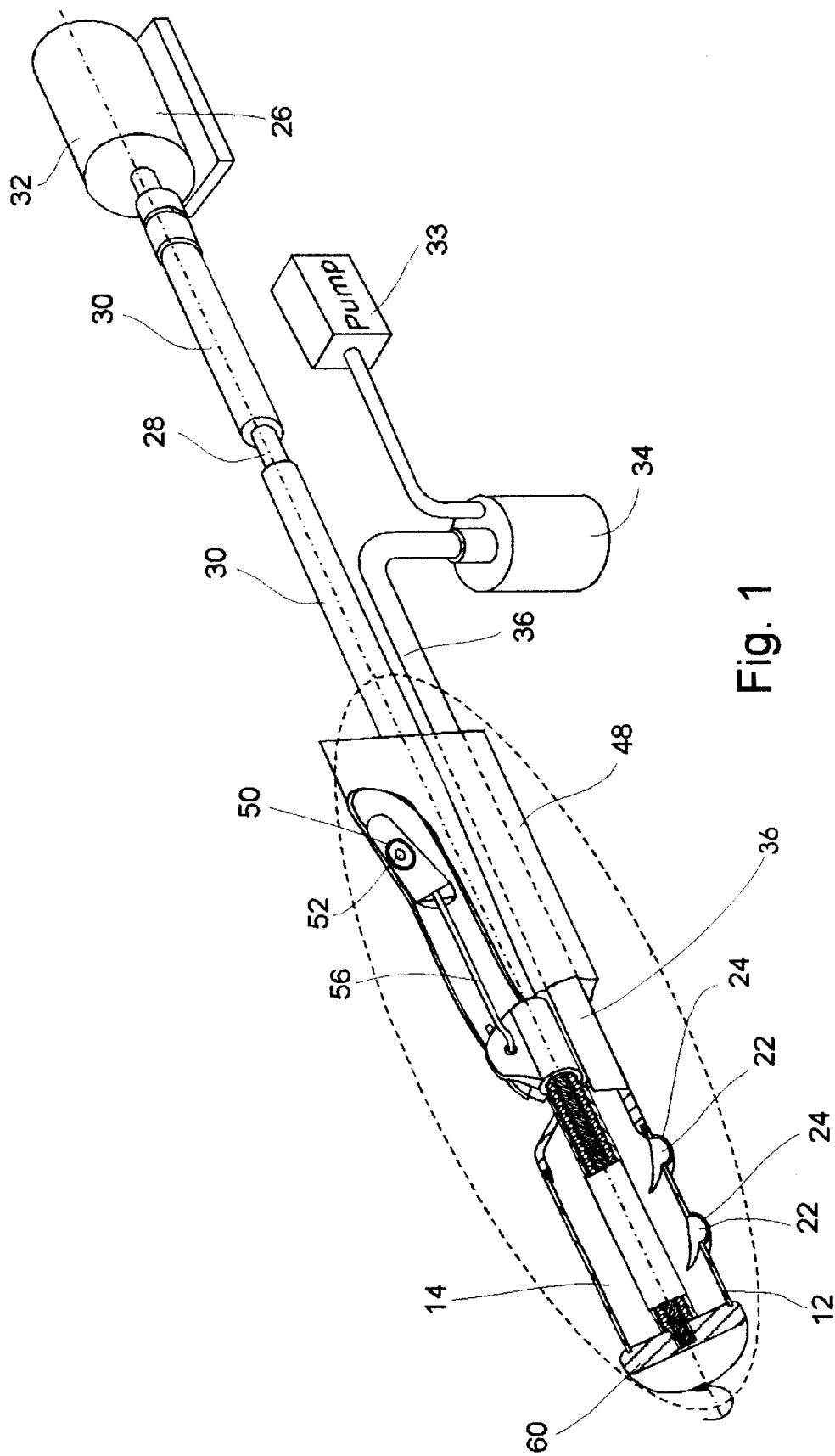
FIG. 1 is a perspective view of a resecting device including a cutaway image of a cannula thereof according to one embodiment of the present invention.

The present invention is of a resecting device and method which can be employed in tissue resection procedures of a variety of body tissues. Specifically, the present invention can be used to dissect and collect (i.e., resect) various tissues from various regions of the body in a precise rapid and efficient manner, such that damage to surrounding tissues and the length of the procedure are both minimized.

The principles and operation of a resecting device and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein and in the claims section that follows the term "resection" refers to a process involving dissection and collection of body tissues.

Thus, according to the present invention there is provided a resecting device for use in tissue removal from a body. Such tissue removal, as effected by the resecting device of the present invention, is typically employed in procedures, such as, but not limited to, urological procedures, e.g., trans-urethral resection of the prostate (TURP), gynecological procedures, gastrointestinal procedures, cardiovascular procedures, neurological procedures and ophthalmologic procedures.

In addition, since the resecting device of the present invention collects the dissected tissue, such device can also be used in various procedures in which tissue biopsy is needed. Such procedures can include, but are not limited to, removal of tissue masses suspected of tumorogenicity.

Figure 2:
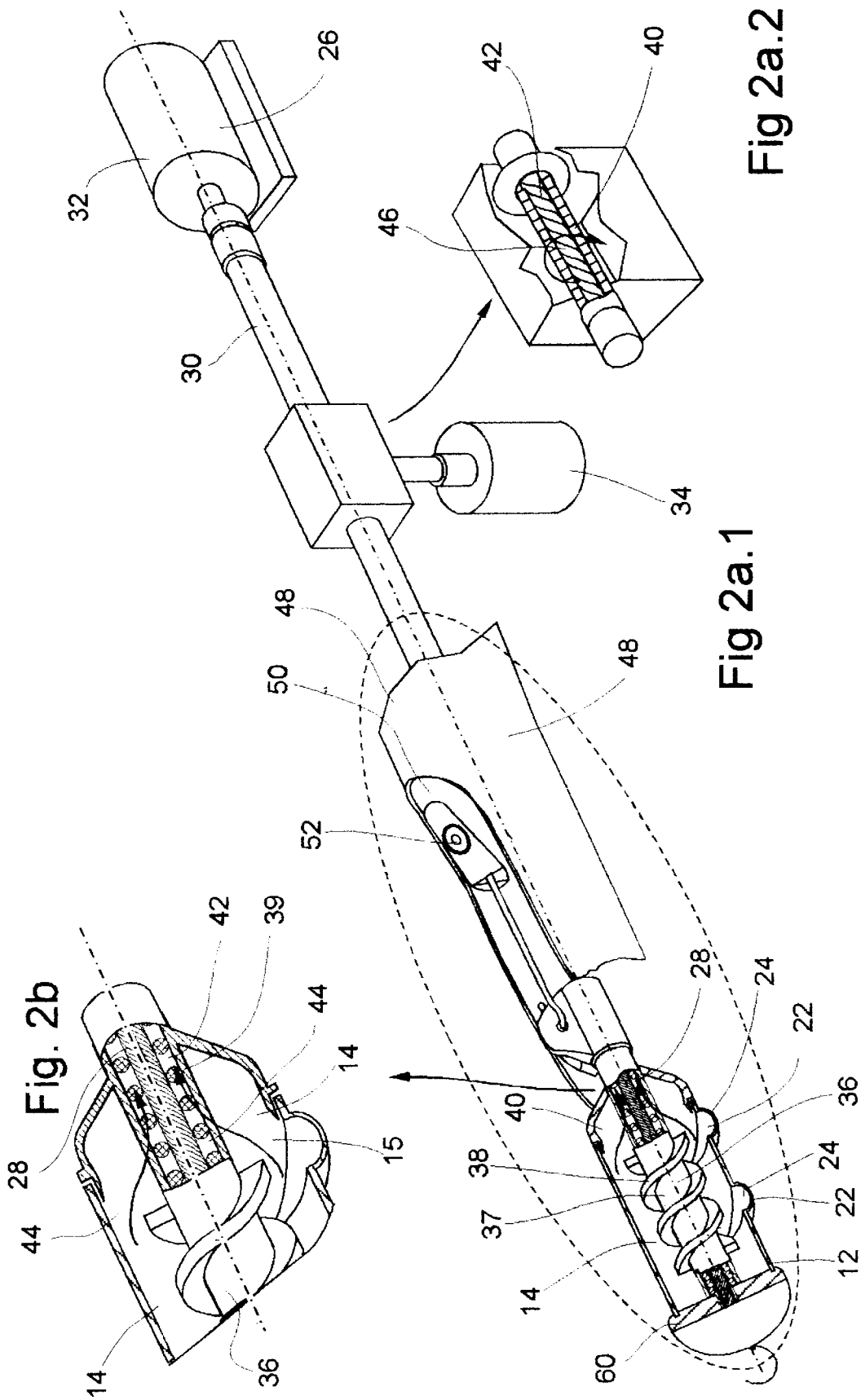
Figure 3:
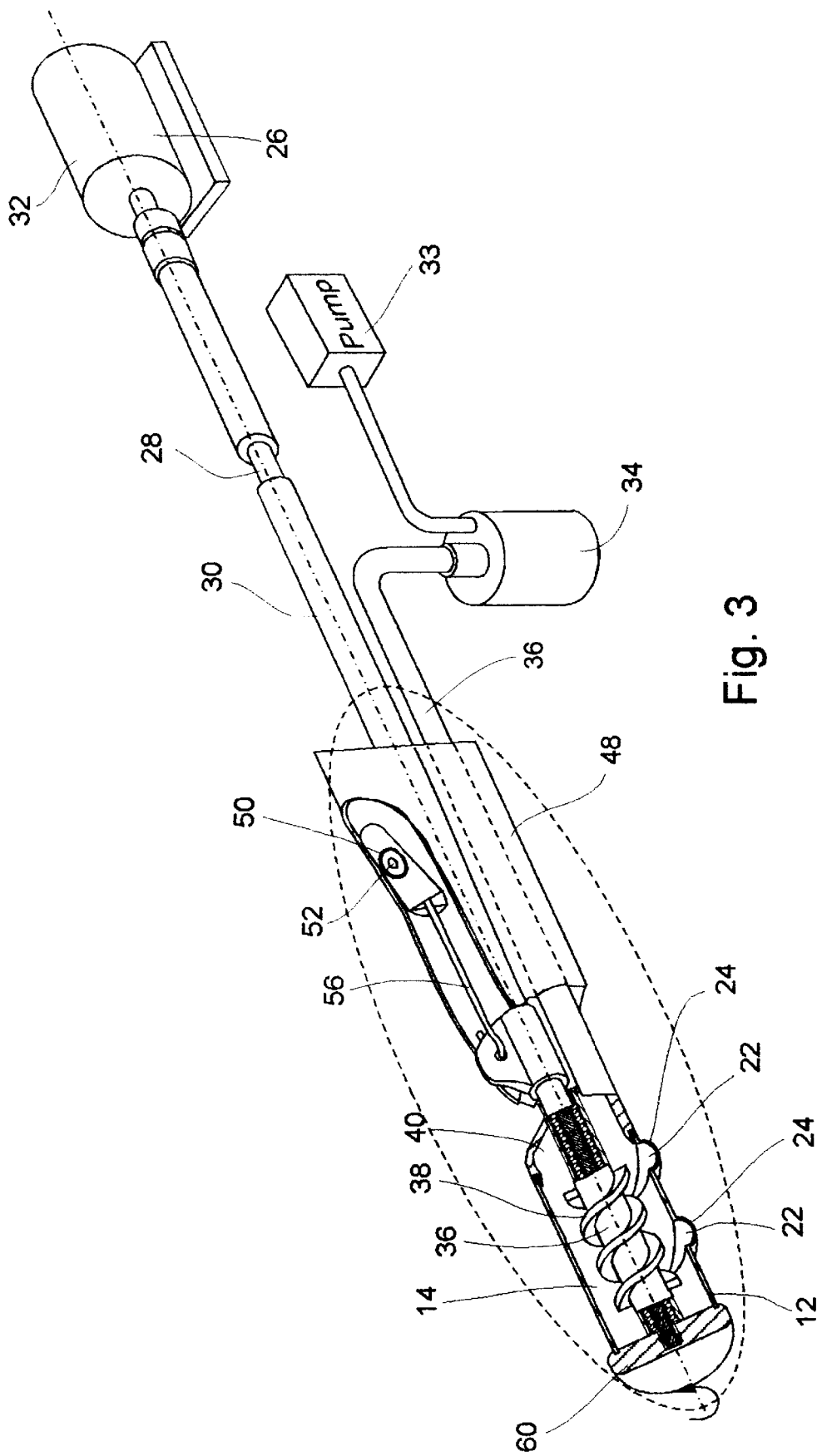
FIG. 3 is a perspective view of a resecting device including a cutaway image of the cannula, according to yet another embodiment of the present invention.

Referring now to the drawings, FIGS. 1–3 illustrate some preferred embodiments of the resecting device according to the present invention, which is referred to hereinbelow as resecting device 10.

Resecting device 10 includes a cannula 12 having a hollow 14. Cannula 12 is sized for introduction into a body, and as such, cannula 12 is preferably between 1 and 20 mm, more preferably between 2 and 7 mm, most preferably between 3 and 6 mm in diameter, depending on the specific application.

In addition, and as specifically shown in FIGS. 4a–g, cannula 12 of resecting device 10 according to the present invention can acquire a variety of shapes and designs, such as, but not limited to, spherical shapes 16, conical shapes 18, and cylindrical shapes 20.

Regardless of its shape, cannula 12 is attachable/detachable onto resecting device 10 through a dedicated coupler 21 which is preferably formed with a holding grove 23 at a distal end thereof. However, other coupling mechanisms, such as pins, are also envisaged. Coupler 21 is designed such that a fixed attachment of cannula 12 according to any of its configurations, as depicted, for example, in FIGS. 4a–g, to resecting device 10 is effected in a removable manner, so as to allow for the selection and employment of a cannula most suitable for any specific application. For example, a conical cannula 18 (shown in FIGS. 4b and 4e–g) can be used in a TURP procedure, in which enlargement and unblocking of a urethral prostate is performed.

As shown in FIGS. 1–5, to effect tissue excision, cannula 12 is preferably formed with cutting openings 22, two of which are shown in FIG. 1-, however any appropriate number of cutting openings is envisaged, from a single opening to several hundreds of openings. Each of cutting openings 22 includes a cutting edge 24 for cutting the tissue to be removed. To this end, cutting edge is made of a material which can provide a high degree of sharpness such as, but not limited to, steel or ceramics. As specifically shown in FIGS. 4e–g, according to one embodiment of the present invention, cutting openings 22 are arranged on a circumference of cannula 12 (several possible arrangements are shown in FIGS. 4e–g), either in the same cutting direction or in an opposing configuration. Alternatively, at least one cutting opening 22 (two are shown in, for example, FIG. 4d) is formed at a proximal end 21 of cannula 12.

Resecting device 10 further includes a rotating mechanism 26 to which cannula 12 is attached. Mechanism 26 can be rotated, for example, by means of an electrical or pneumatic motor. Rotating mechanism 26 and the controls thereof can be housed within a handpiece 32 which is used to operate device 10 by directing cannula 12 to a specific region in the body. Alternatively and presently preferably, rotating mechanism 26 is mounted on a carriage which does not form an integral part of resecting device 10. In both configurations, however, cannula 12 is preferably connected to rotating mechanism 26 through a dedicated driving shaft, as is further described hereinunder.

Thus, rotating mechanism 26 is connected through a shaft 28 to cannula 12 and provides cannula 12 with rotary motion around a longitudinal axis thereof. At least a portion of shaft 28 is preferably covered by a protecting sleeve 30 for protecting the body from the rotary motion of shaft 28. In addition, both shaft 28 and sleeve 30 are preferably flexible, so as to enable freedom in guiding cannula 12 within the body.

To this end, both sleeve 30 and shaft 28 are composed of flexible materials and/or structures, such as, but not limited to, plastics, polymers and metals, in, for example a spiral spring design. Alternatively, sleeve 30 and shaft 28 can be articulated.

Cannula 12 is preferably provided with a rotary motion in one direction around the longitudinal axis thereof, or alternatively cannula 12 can be rotated in a reciprocating motion. In the latter case, cannula 12 is integrated in a resecting device provided with a reciprocating motion and is formed with opposing cutting openings 22 (as specifically shown in FIG. 4e), such that, for example, a specific tissue within the body can be excised without inflicting damage on surrounding tissues.

Preferably, resecting device 10 is provided with controls housed within handpiece 32, such that a user can select between modes of unidirectional rotary motion or reciprocating rotary motion.

A potentiometer is preferably employed for controlling the speed of rotation.

When cannula 12 is contacted with a tissue and is rotated, cutting edges 24 of cutting openings 22 are designed so as to dissect the tissue and direct the dissected tissue through the openings into hollow 14 of cannula 12. As such, cutting openings 22 are preferably "tear drop"-shaped and are formed each with a semicircular and protruding opening, which forms cutting edge 24. Tissue collected within hollow 14 can be used for later analysis.

Figure 6:
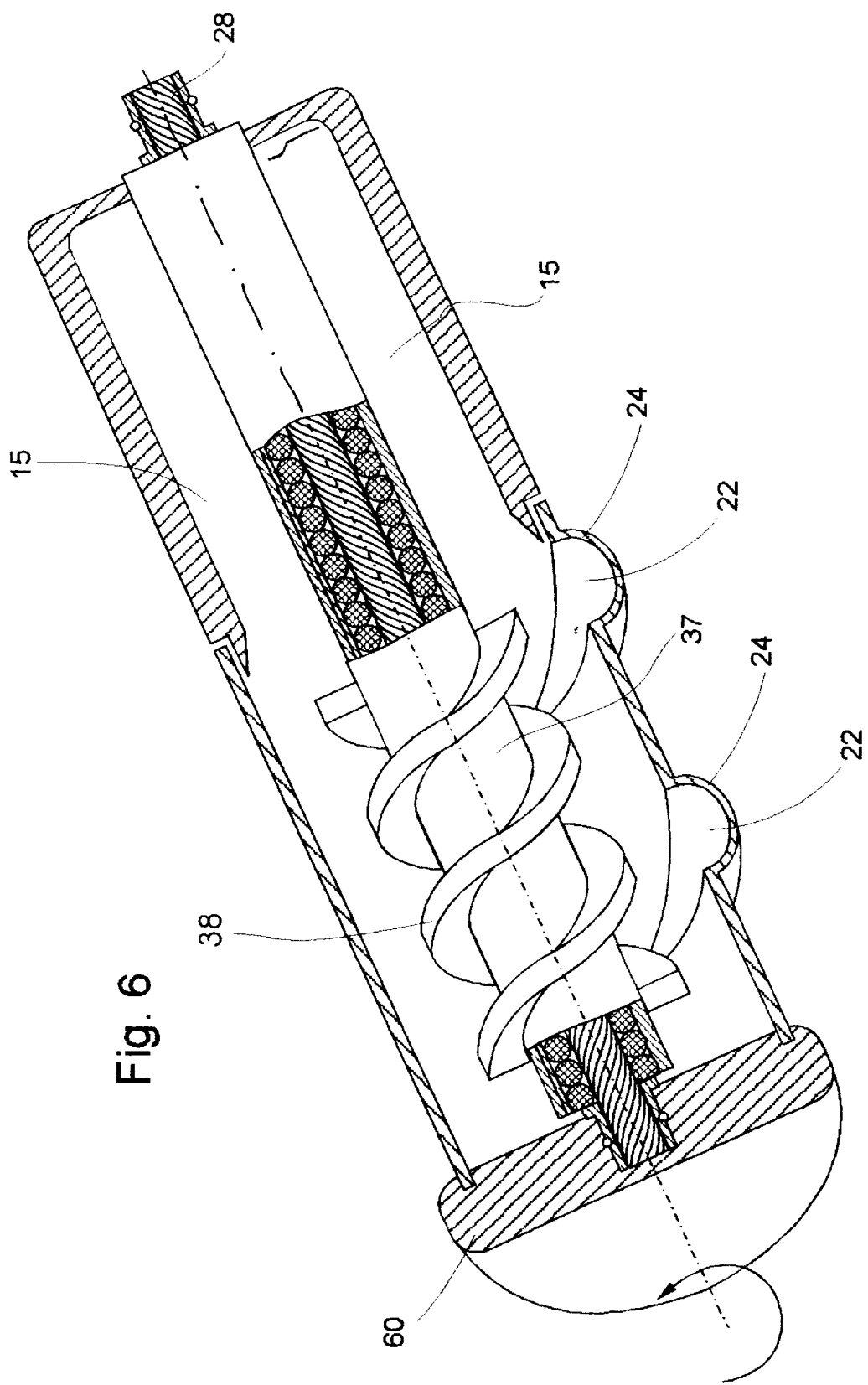
FIG. 6 is a cross sectional view of a cannula serving also as a tissue collecting chamber, according to yet another embodiment of the present invention.

According to one embodiment of the present invention, and as specifically shown in FIG. 6, tissue collected by cannula 12 is transported to a distal portion 15 of hollow 14 and collected within distal portion 15 of hollow 14 until cannula 12 is removed from the body, such that resected tissues can be collected by a user and cannula 12 disposed or reused thereafter.

To further assist in the collection of tissue within distal portion 15, cannula 12 is preferably further provided with a conveying mechanism in hollow 14. The operation of such a conveying mechanism and specific examples thereof are provided hereinunder.

According to another embodiment of the present invention, resecting device 10 further includes a tissue collecting chamber 34. Chamber 34 is in fluid communication with hollow 14 of cannula 12, such that tissue collected in hollow 14 by and through cutting openings 22 is transported to chamber 34. As further detailed hereinunder, transporting of the dissected tissue to chamber 34 is effected by one of several alternative mechanisms.

As shown in FIG. 1, tissue collected within hollow 14 of cannula 12 is transported into chamber 34 through a tube 36 by a pumping action which is provided by a pump 33. According to this configuration, tube 36 is connected to hollow 14 outside of sleeve 30. Alternatively, tube 36 can extend within a space formed between sleeve 30 and shaft 28.

In yet another configuration, and as specifically shown in FIGS. 2a–b, 3, 5 and 6, resecting device 10 further includes a conveying mechanism 37. Conveying mechanism 37 preferably includes an Archimedes screw 38 which is engaged within hollow 14 of cannula 12. To operate as a conveying mechanism, Archimedes screw 38 is either stationary or it is counter-rotated relative to cannula 12. Counter-rotating screw 38 can be effected by a dedicated gear, belt, chain and/or clutch mechanism.

As specifically shown in FIG. 5, according to a preferred embodiment, if selected stationary, Archimedes screw 38 is formed hollow and around shaft 28 which is rotating about coil 39, such that dissected tissue collected within hollow 14 of cannula 12 is transported via the contours of Archimedes screw 38 to distal portion 15 thereof. Dissected tissue accumulating at distal portion 15 of hollow 14 is then transported to chamber 34 by the pumping action of pump 33 through tube 36 (best seen in FIG. 3).

Alternatively, according to another preferred embodiment of the present invention and as specifically shown in FIG. 6 and mentioned above, conveying mechanism 37, which in this case is realized as Archimedes screw 38, is provided within hollow 14 of cannula 12 such that resected tissue, when accumulating in hollow 14 is conveyed to distal portion 15 of hollow 14 which serves in this case as a collection chamber. Thus, according to this embodiment of the present invention, when a resection procedure is completed, device 10 is removed from the body, following which cannula 12 is detached from device 10 and the tissue collected within recovered for analysis. Alternatively, according to another preferred embodiment of the present invention, and as specifically shown in FIGS. 2a.1–2a.2 and FIG. 2b, a space 42 farmed between shaft 28 and sleeve 30 which covers shaft 28, and which extends from hollow 14 to chamber 34, serves as a channel for directing resected tissue therethrough from hollow 14 and into chamber 34. According to a preferred embodiment, a coil 39 which resides within space 42 serves an Archimedes screw like capacity. In addition, space 42 is provided with openings 44 communicating with hollow 14, and openings 46 communicating with chamber 34, such that fluid communication between hollow 14 and chamber 34 though space 42 is established. In this case, tissue driven by Archimedes screw 38 to distal end 15 of hollow 14 is forced into space 42 through openings 44. While in space 42, tissue is conveyed to collection chamber 34 through the Archimedes screw like action of coil 39.

According to another preferred embodiment of the present invention, resecting device 10 further includes an imaging device 50. As shown in FIGS. 1–3, imaging device 50 is preferably housed in a housing 48 located over sleeve 30 distal and adjacent to cannula 12. Imaging device 50 serves for monitoring a procedure performed by resecting device 10. To this end, imaging device 50 includes a viewing aperture 52 which serves for receiving an image from a region within the body. Viewing aperture 52 can be optically coupled to a variety of imaging means, such as, but not limited to, a monitor, a screen, a camera, a video, a microscope or a viewing lens. Preferably such coupling is established through light guides, such as optic fibers, although other configurations are envisaged. Device 50 preferably further includes a light source, which serves for lighting the imaged region within the body.

Figure 7:
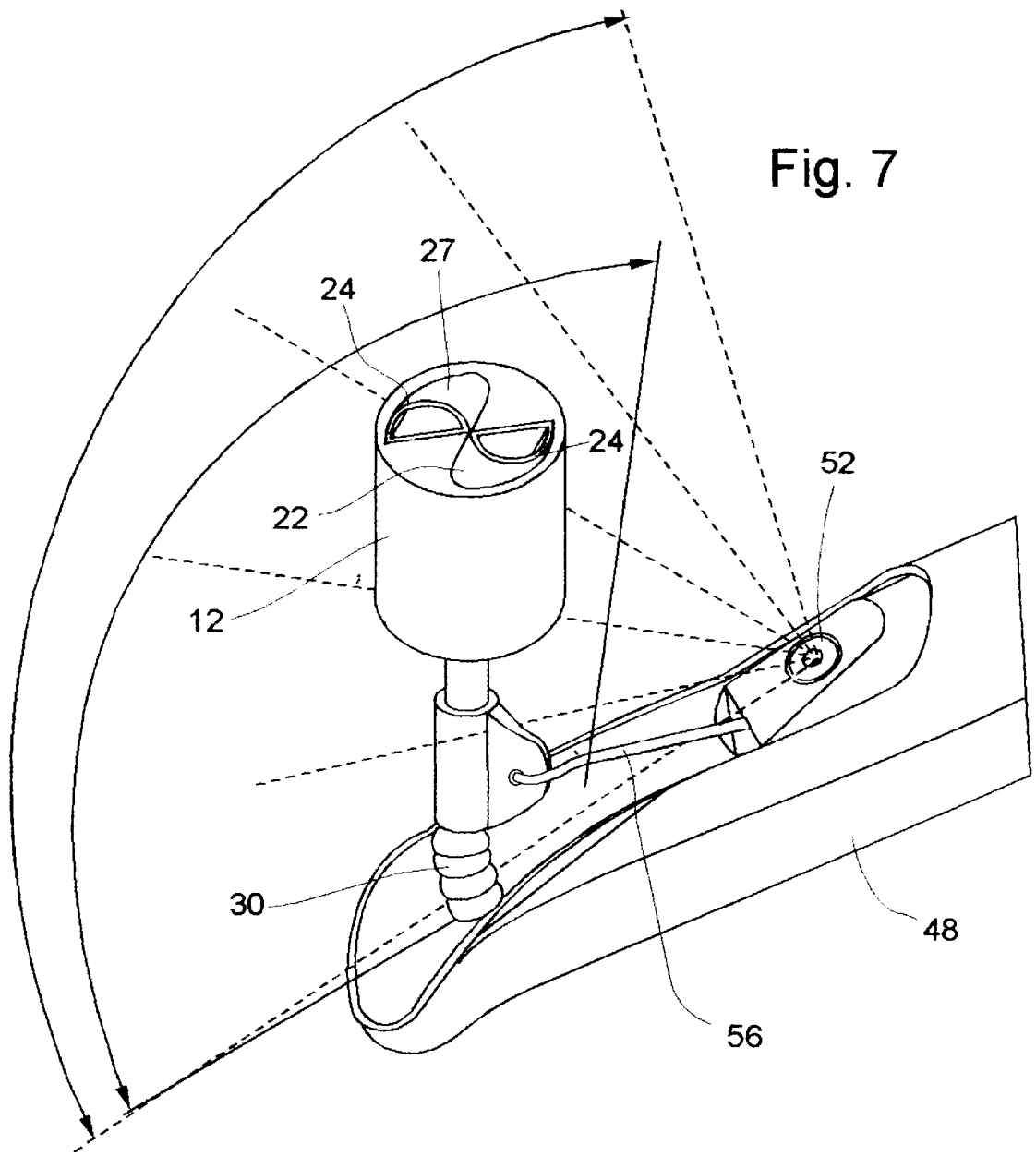
FIG. 7 is a perspective view of a resecting device of the present invention shown to be positionally effected.

According to a preferred embodiment of the present invention, resecting device 10 includes a guiding mechanism 56. In the example of FIGS. 1–2 and 7, mechanism 56 is realized as a member connecting sleeve 30 adjacent to cannula 12 with housing 48. Mechanism 56 is operated via handpiece 32 to effect positional orientation (one such orientation is shown in FIG. 7) between mechanism 56 and sleeve 30 such that cannula 12 can be spatially oriented in a plurality of positions relative to handpiece 32, thus allowing guiding and positioned of cannula 12 in various body regions.

According to another preferred embodiment of the present invention, resecting device 10 includes a heating device 60. Heating device 60 serves for heating the tissue in the area of resection, such that blood homeostasis is achieved. To this end, heating device 60 is heated to a temperature preferably in the range of 50–1000° C., more preferably in the range of 100–500° C., most preferably in the range of 150–300° C.

Figure 8:
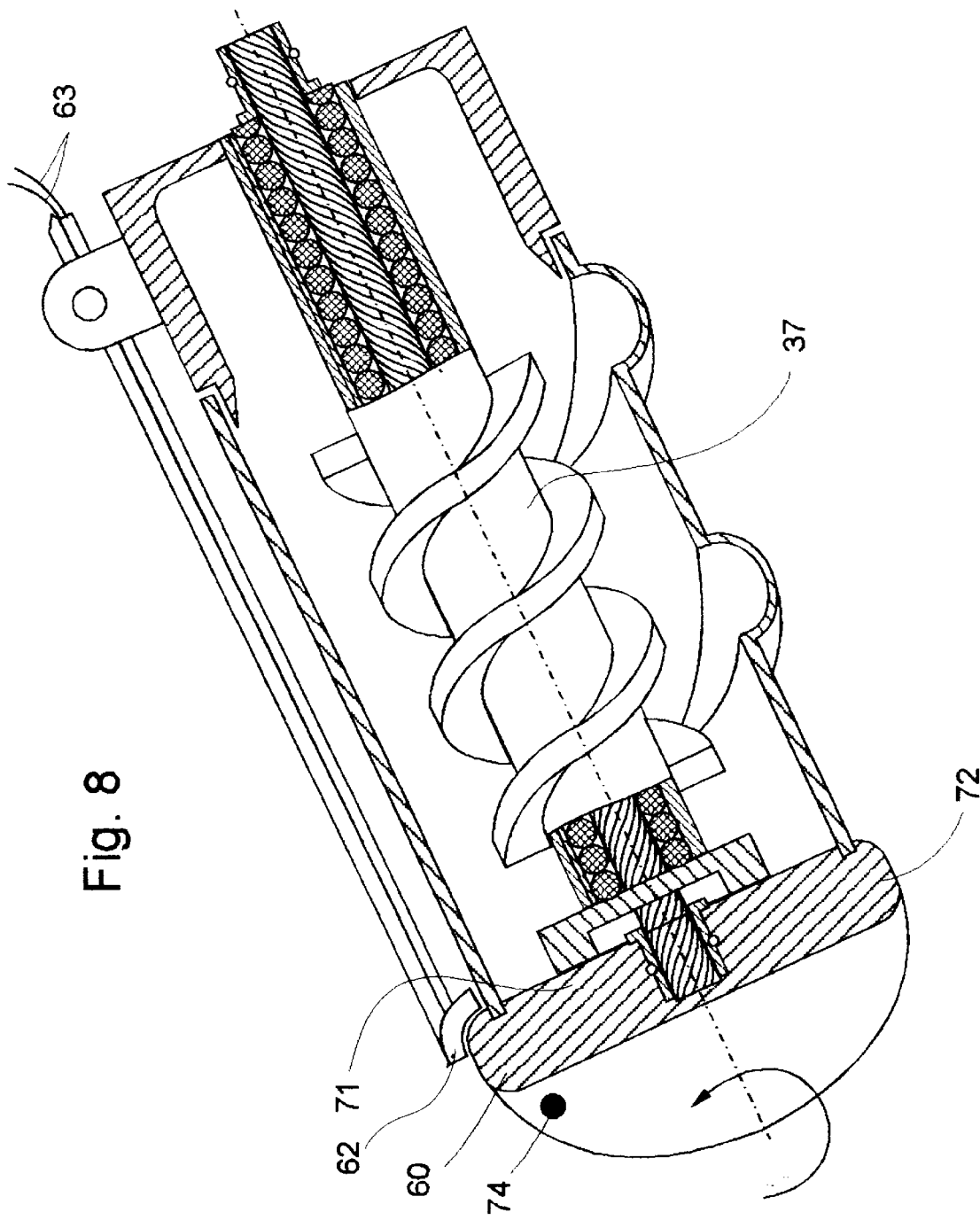
FIGS. 8–9 are cross sectional views of cannulas supplemented with a friction based heating device according to yet another embodiments of the present invention.

In the example of FIG. 8, heating device 60 includes a friction element (e.g., pad) 62 which can be brought in or removed from contact with a dedicated portion of cannula 12. When cannula 12 rotates and region 71 of heating device 60 is contacted with element 62 sufficient heat is generated in device 60 such that when contacted with a bleeding tissue, homeostasis is effected. Alternatively cannula 12 is formed of a good heat conducting material, and as such heat from device 60 is conducted via cannula 12 to the tissue to cause horneostasis. Contacting stationary friction element 62 with cannula 12 is controlled preferably via wires 63 and through handpiece 32. The direction and dissipation of the heat generated can be controlled by appropriately selecting materials with suitable heat conductivity and friction coefficients. For example, providing the tip of cannula 12 with a good heat conductor and providing element 62 as a poor heat conductor will result in directing the generated heat through the tip of cannula 12 to the tissue to effect blood homeostasis therein.

Figure 9:
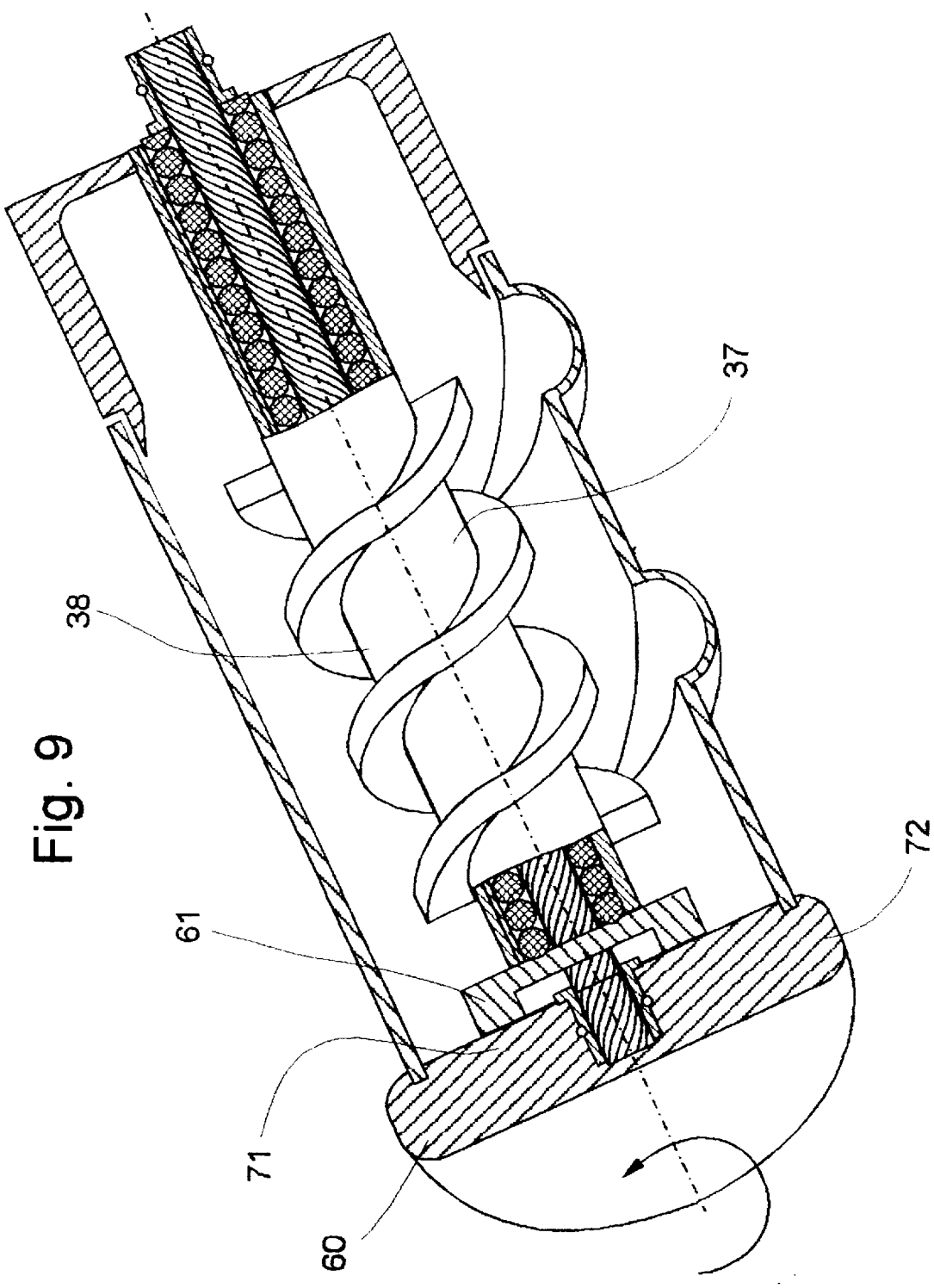

Yet another example of a friction operated heat device 60 is shown in FIG. 9. According to this configuration, a friction disk 61 which can be connected to or form an integral part of Archimedes screw 38 (which in this embodiment is selected stationary) or sleeve 30, is selectively engagable by a user operated mechanism, preferably operated from handpiece 32, against region 71 of the rotating cannula 12, thereby generating heat in a fashion similar to as described above.

Figure 10:
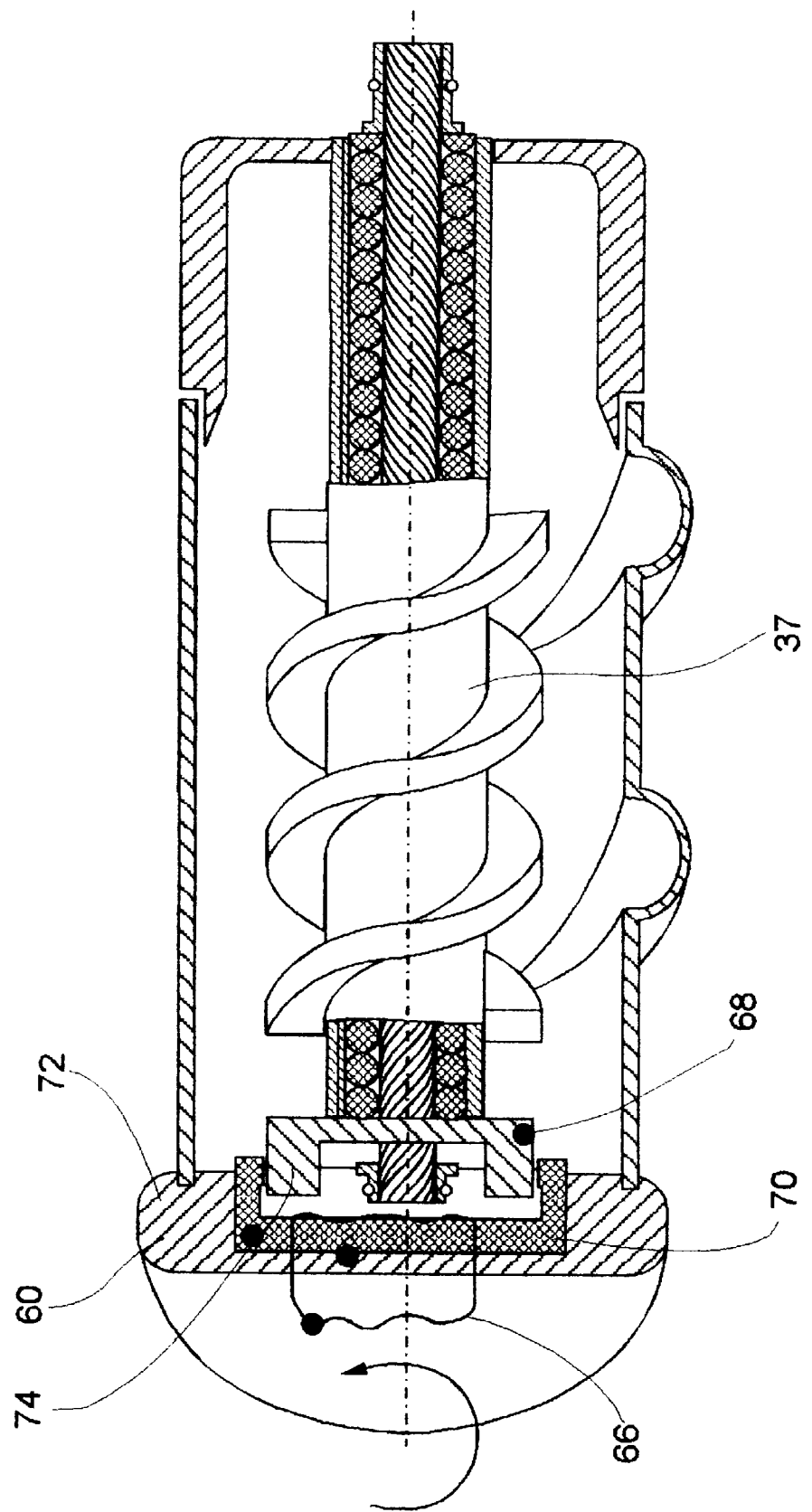
FIG. 10 is a cross sectional view of a cannula supplemented with a wire based heating device according to still another embodiment of the present invention.

Alternatively, and as shown in FIG. 10, heating device 60 includes a heating wire 66. Heating wire 66 is provided with electricity generated from the rotating motion of a magnet 68 positioned in cannula 12 juxtaposed to a fixed ferrous material 70 which preferably includes a plurality of current circuits to increase heat production, and connected to heating wire 66. Optionally, heating wire 66 is provided with direct current from a battery and user controls located within handpiece 32.

According to another preferred embodiment of the present invention and as further shown in FIG. 10, resecting device 10 further includes a temperature sensor 74, which is preferably located on a non-rotating portion of cannula 12 adjacent to a proximal portion 72 thereof and not in contact with heating device 60. Temperature sensor 74 monitors the temperature within the region of resection, such that efficient homeostasis is achieved yet thermal damage is not inflicted upon surrounding tissues. To this end, output from temperature sensor 74 can be linked to heating device 60, such that the temperature sensor 74 senses exerts control over the heating process, or alternatively temperature sensor 74 can inform a user of the temperature at the region of interest, such that the user can then modulate the heating process accordingly.

The present invention has major advantages as compared with prior art resecting devices. The resecting device according to the present invention is capable of not only dissecting and collecting the dissected tissue, the resecting device according to the present invention further provides for built-in blood homeostasis. In addition, by performing a rotational movement, a large volume of tissue is collectable within a shorter time period. Furthermore, the resecting device according to the present invention allows the removal of tissues of various shapes, e.g., tissue underlining a tube or an orifice, etc., which is much less applicable using prior art translating devices.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A resecting device for use in tissue removal, comprising:
    (a) a cannula having a hollow and a longitudinal axis, said cannula being sized for introduction into a body and formed with at least one cutting opening having a cutting edge;
    (b) a rotating mechanism connectable through a shaft to said cannula for rotating said cannula around said longitudinal axis thereof, such that when contacted with a tissue and rotated, said cutting edge of said at least one cutting opening dissects the tissue and directs the dissected tissue through said opening and into said hollow of said cannulal; and
    (c) a heating device, said hearing device being for heating the tissue, said heating device including a friction element being contactable with a portion of said cannula, so as to generate heat thereat.

2. The resecting device of claim 1, wherein said rotating mechanism is for rotating said cannula in reciprocal rotary motion.

3. The resecting device of claim 2, wherein said cannula is formed with at least two cutting openings, said at least two cutting openings are positioned in an opposing configuration on at least a portion of said cannula.

4. The resecting device of claim 1, further comprising a non-rotating protective sleeve covering at least a portion of said shaft.

5. The resecting device of claim 4, wherein both said sleeve and said shaft are flexible, so as to assist in spatial positioning of said cannula in the body.

6. The resecting device of claim 1, further comprising a handpiece, said handpiece being for guiding said cannula into a preselected region of the body.

7. The resecting device of claim 6, wherein said handpiece includes a motor connected to said shaft, said motor serves for rotating said cannula.

8. The resecting device of claim 1, further comprising a tissue collecting chamber, said chamber being in fluid communication with said hollow such that tissue collected in said hollow is transportable to said chamber.

9. The resecting device of claim 8, wherein said chamber is in fluid communication with said hollow through a tube.

10. The resecting device of claim 8, wherein said chamber is in fluid communication with said hollow through a channel formed between said shaft and a sleeve covering said shaft.

11. The resecting device of claim 8, further comprising a pump, said pump being in fluid communication with said collecting chamber and being for pumping the dissected tissue from said cannula and into said collecting chamber.

12. The resecting device of claim 8, further comprising a conveying mechanism in said hollow of said cannula, said conveying mechanism being for conveying the dissected tissue from said cannula to said collecting chamber.

13. The resecting device of claim 12, wherein said conveying mechanism includes an Archimedes screw.

14. The resecting device of claim 13, wherein said Archimedes screw is counter rotatable relative to said cannula.

15. The resecting device of claim 13, wherein said Archimedes screw is stationary.

16. The resecting device of claim 1, wherein a distal portion of said hollow serves as a tissue collecting chamber.

17. The resecting device of claim 16, further comprising a conveying mechanism in said hollow of said cannula, said conveying mechanism being for conveying the dissected tissue into said distal portion of said hollow.

18. The resecting device of claim 17, wherein said conveying mechanism includes an Archimedes screw.

19. The resecting device of claim 1, further comprising an imaging system for intrabody monitoring a procedure being effected by the resecting device.

20. The resecting device of claim 1, wherein said cannula is formed with a plurality of cutting openings, said plurality of cutting openings are circumferencely positioned on at least a portion of said cannula.

21. The resecting device of claim 1, wherein said cannula has a shape selected from the group consisting of a cone-shape, a cylindrical shape and a spherical shape.

22. The resecting device of claim 1, wherein said heating device includes a heating wire.

23. The resecting device of claim 1, further comprising a temperature sensor for sensing said heat.

24. A surgical procedure of tissue excision in a preselected region in a body, the procedure comprising the steps of:
    (a) providing a resecting device, including a cannula having a hollow and a longitudinal axis, said cannula being sized for introduction into the body and being formed with at least one cutting opening having a cutting edge, said resecting device further including a heating device, said heating device being for heating a tissue, said heating device including a friction element being contactable with a portion of said cannula, so as to generate heat thereat;
    (b) inserting said cannula into the preselected region in the body; and
    (c) contacting said cannula with a tissue to be excised and rotating said cannula via a rotating mechanism, such that said cutting edge of said at least one cutting opening dissects the tissue and directs the dissected tissue through said opening and into said hollow.

25. The surgical procedure of claim 24, selected from the group consisting of a urological procedure, a gynecological procedure, a gastrointestinal procedure, a cardiovascular procedure, a neurological procedure and an ophthalmologic procedure.

26. The resecting device of claim 22, further comprising a temperature sensor for sensing said heat.

27. The resecting device of claim 22, wherein said heating device includes a heating wire.

28. A resecting device for use in tissue removal, comprising:
    (a) a cannula having a hollow and a longitudinal axis, said cannula being sized for introduction into a body and formed with at least one cutting opening having a cutting edge;
    (b) a rotating mechanism connectable through a shaft to said cannula for rotating said cannula around said longitudinal axis thereof, such that when contacted with a tissue and rotated, said cutting edge of said at least one cutting opening dissects the tissue and directs the dissected tissue through said opening and into said hollow of said cannula, said shaft including at least one bendable portion;
    (c) a guiding mechanism for bending said at least one bendable portion of said shaft to thereby change a positional orientation between said cannula and said shaft, for allowing flexibility in guiding and positioning of said cannula; and
    (d) a heating device for heating the tissue, said heating device includes a friction element being contactable with a portion of said cannula, so as to generate heat thereat.

29. The resecting device of claim 28, wherein said rotating mechanism is for rotating said cannula in reciprocal rotary motion.

30. The resecting device of claim 29, wherein said cannula is formed with at least two cutting openings, said at least two cutting openings are positioned in an opposing configuration on at least a portion of said cannula.

31. The resecting device of claim 28, further comprising a handpiece said handpiece being for guiding said cannula into a preselected region of the body.

32. The resecting device of claim 31, wherein said handpiece includes a motor connected to said shaft, said motor serves for rotating said cannula.

33. The resecting device of claim 28, further comprising a tissue collecting chamber, said chamber being in fluid communication with said hollow such that tissue collected in said hollow is transportable to said chamber.

34. The resecting device of claim 33, further comprising a pump, said pump being in fluid communication with said collecting chamber and being for pumping the dissected tissue from said cannula and into said collecting chamber.

35. The resecting device of claim 33, wherein said chamber is in fluid communication with said hollow through a channel formed between said shaft and a sleeve covering said shaft.

36. The resecting device of claim 33, wherein said chamber is in fluid communication with said hollow through a tube.

37. The resecting device of claim 33, further comprising a conveying mechanism in said hollow of said cannula, said conveying mechanism being for conveying the dissected tissue from said cannula to said collecting chamber.

38. The resecting device of claim 37, wherein said conveying mechanism includes an Archimedes screw.

39. The resecting device of claim 38, wherein said Archimedes screw is counter rotatable relative to said cannula.

40. The resecting device of claim 38, wherein said Archimedes screw is stationary.

41. The resecting device of claim 28, wherein a distal portion of said hollow serves as a tissue collecting chamber.

42. The resecting device of claim 41, further comprising a conveying mechanism in said hollow of said cannula, said conveying mechanism being for conveying the dissected tissue into said distal portion of said hollow.

43. The resecting device of claim 42, wherein said conveying mechanism includes an Archimedes screw.

44. The resecting device of claim 28, further comprising a non-rotating protective sleeve covering at least a portion of said shaft.

45. The resecting device of claim 44, wherein both said sleeve and said shaft are flexible, so as to assist in spatial positioning of said cannula in the body.

46. The resecting device of claim 28, further comprising an imaging system for intrabody monitoring a procedure being effected by the resecting device.

47. The resecting device of claim 28, wherein said cannula is formed with a plurality of cutting openings, said plurality of cutting openings are circumferencely positioned on at least a portion of said cannula.

48. The resecting device of claim 28, wherein said cannula has a shape selected from the group consisting of a cone-shape, a cylindrical shape and a spherical shape.

* * * * *